United States Patent [19]

Shook, Jr.

[11] 4,082,811

[45] Apr. 4, 1978

[54] RECOVERY OF METAL AND TRIARYLBORANE CATALYST COMPONENTS FROM OLEFIN HYDROCYANATION RESIDUE

[75] Inventor: Howard Everett Shook, Jr., Orange, Tex.

[73] Assignee: E. I. Du Pont de Nemours and Company, Wilmington, Del.

[21] Appl. No.: 771,064

[22] Filed: Feb. 23, 1977

[51] Int. Cl.$^2$ .................. C07F 5/02; C07F 15/04; C01C 31/11; C07C 120/02
[52] U.S. Cl. .................. 260/606.5 B; 252/412; 260/465.8 R; 260/465.9; 423/143; 423/364
[58] Field of Search .................. 252/412, 420, 431 P; 260/465.8 R, 439, 606.5 B; 423/143, 364

[56] References Cited

U.S. PATENT DOCUMENTS

| | | | |
|---|---|---|---|
| 3,496,218 | 2/1970 | Drinkard, Jr. | 260/465.8 R |
| 3,651,146 | 3/1972 | Von Schriltz | 260/606.5 B |
| 3,652,641 | 3/1972 | Druliner | 260/465.8 R |
| 3,766,241 | 10/1973 | Drinkard, Jr. | 260/465.8 R |
| 3,818,068 | 6/1974 | Wells | 260/439 R |
| 3,859,327 | 1/1975 | Wells | 252/431 P |
| 3,864,380 | 2/1975 | King et al. | 260/465.8 R |

Primary Examiner—Winston A. Douglas
Assistant Examiner—P. E. Konopka

[57] ABSTRACT

Process for the recovery of catalyst components from a catalyst residue, e.g., a residue obtained from the hydrocyanation of olefins, e.g., butadiene, using a zerovalent nickel complex promoted with a triarylborane as a catalyst by contacting the residue with an essentially aqueous solution of nitrogen-containing base, e.g., ammonium hydroxide to form and precipitate the amine adduct of the triarylborane, while maintaining other catalyst components in solution and thereafter separating the precipitate from the resultant solution. Nickel can be separated from the resultant solution by reducing the concentration of amine in the solution to thereby precipitate a nickel cyanide complex, e.g., nickel (II) cyanidemonoammine.

4 Claims, 1 Drawing Figure

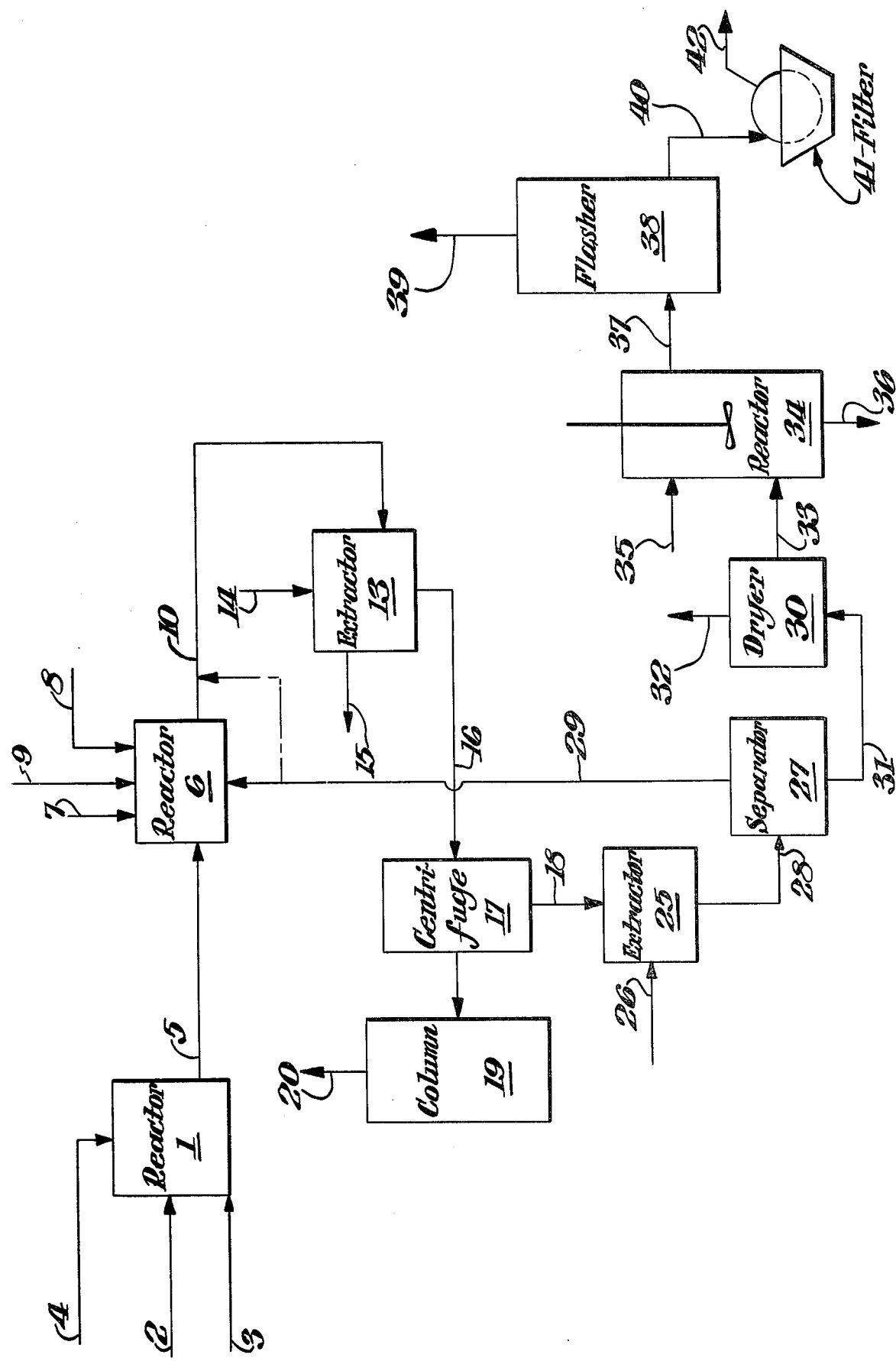

RECOVERY OF METAL AND TRIARYLBORANE CATALYST COMPONENTS FROM OLEFIN HYDROCYANATION RESIDUE

BACKGROUND OF THE INVENTION

1. Field of the Invention

The present invention relates to the recovery of catalyst components from process residue and more particularly, to a process for recovery of triarylboranes and metals from the process residue obtained from the hydrocyanation of olefins, e.g., from the preparation of adiponitrile by hydrocyanation of butadiene using nickel or palladium complexes as catalysts with triphenylborane as the catalyst promoter.

2. Description of the Prior Art

A general disclosure of typical processes to which the present invention can be applied is found in the publication entitled "Hexamethylene Diamine" in The Process Economics Program Report No. 31-A, Stanford Research Institute, Menlo Park, C.A.; September, 1972. More particularly, the hydrocyanation process to which the present invention can be applied is disclosed in U.S. Pat. Nos. 3,496,215 issued on Feb. 17, 1970, 3,496,218 issued on Feb. 17, 1970, 3,542,847 issued on Nov. 24, 1970, and 3,752,839 issued on Aug. 14, 1973. The residue from the above-disclosed process is obtained by removing the substantial portion of desired products, unreacted materials and intermediates from the reactor effluent, separating solvent and other volatiles from the resultant stream for recycle to the reactor and thereafter obtaining a concentrated waste stream.

The solids in this concentrated waste stream are principally catalyst residues which represent a significant economic penalty if not recovered. The present invention is directed to the recovery of the catalyst and catalyst promoter in the waste stream.

Some chemistry has been disclosed for the reactions involving the ammonia adduct of triarylborane. Ammonia displacement from this adduct by reacting the adduct with quaternary ammonium fluoride and hydroxide salts in the presence of ethanol to produce complex salts is disclosed by D. L. Fowler and C. A. Kraus, *J. Am Chem. Soc.*, 62, 1143 (1940). This adduct was reacted with dry hydrochloric acid in the presence of ether by Mikhailov et al. [Izvest. Akad. Nauk S.S.S.R., Otdel. Kimm. Nauk, 812 (1957)] to produce triphenylborane and ammonium chloride. G. Wittig et al. [Ann. Chem., 573, 195 (1951)] produced triphenylborane by thermally decomposing $(CH_3)_3NH + B(C_6H_5)_4—$ and further disclose the preparation of the sodium hydroxide salt of triphenylborane by fusion of the borane with sodium hydroxide and the reaction of the salt with ammonium chloride or hydroxide to yield $\phi_3—B.NH_3$. The borane was also reacted with sodium cyanide to yield a compound postulated to have the formula $[\phi_3(CN)B]Na$.

SUMMARY OF THE INVENTION

Process for the recovery of catalyst components from a catalyst residue which residue is obtained from the hydrocyanation of olefins using a catalyst comprising zero-valent nickel complex promoted with a triarylborane and comprises nickel cyanide, triarylborane and complexes of the foregoing. The process involves contacting the residue with an aqueous solution containing at least 10 and preferably 15–40 moles of a nitrogen-containing base, e.g., ammonia per mole of boron plus nickel while maintaining the concentration of said ammonia at at least 6% and preferably 15–25% to maintain the nickel in solution and to form and precipitate the ammonia adduct of said triarylborane and thereafter separating the precipitate from the resultant solution. In a preferred embodiment, the temperature is maintained in the range 90°–110° C for a period of at least 30 minutes while the residue is in contact with the aqueous ammonia solution.

BRIEF DESCRIPTION OF THE DRAWING

The drawing attached hereto and made a part of this specification is a schematic hydrocyanation process which produces a waste stream and the process of the present invention as applied to that stream.

DETAILED DESCRIPTION OF THE INVENTION

The process of the present invention is applied to a waste stream from a process which involves the direct addition of two molecules of hydrogen cyanide to a molecule of butadiene thereby producing adiponitrile. The process is conducted in two steps. With reference to the drawing, the first step (reactor 1) involves the addition of one molecule of hydrogen cyanide (stream 2) to dry butadiene (stream 3) in the presence of a catalyst (stream 4) consisting of zero-valent nickel usually in the form of a nickel tetrakis-tritolylphosphite, to produce a mixture of cis- and trans-3-pentenenitrile and 4-pentenenitrile. This reaction mixture is withdrawn from reactor 1 via line 5, treated to remove impurities and then introduced into reactor 6 along with additional HCN (line 7), ligand (line 8) and triarylborane catalyst promoter such as triphenylborane (line 9). In this reaction which can be conducted in one or more steps, 4-pentenenitrile is formed by the in situ isomerization of 3-pentenenitrile. The 4-pentenenitrile is then converted to adiponitrile by the addition of one molecule of HCN. The effluent from the reactor 6 is passed to extractor 13 and there contacted with cyclohexane (line 14). The cyclohexane extractant (line 15) is subsequently directed to further treatment for product recovery. During the hydrocyanation as described as hereinabove a portion of the zero-valent nickel catalyst is oxidized to nickel cyanide which is insoluble in the reaction medium and which forms insoluble complexes with the triarylborane. The tails from the extraction vessel (line 16) contain such complexes which are subsequently separated from the tails (line 16) by centrifuge 17. A typical analysis of this sludge is set forth below in Table I.

TABLE I

| SLURRY COMPOSITION (% by weight) | |
| --- | --- |
| Triphenylborane ($\phi_3B$) | 57 |
| Ni(CN)$_2$ | 13 |
| Adiponitrile (ADN) | 22 |
| Methylglutaronitrile (MGN) | 2 |
| Pentenenitriles (PN) | 3 |
| Cyclohexane | 3 |
| (Balance - Miscellaneous Organics) | |

The liquid discharge from centrifuge 17 is distilled in column 19 to recover residual 3-pentenenitrile, cyclohexane and other volatiles overhead (line 20). Stream 18 is passed to extractor 25 where it is thoroughly contacted with mono-olefinically unsaturated nitrile introduced via line 26. The solvent is advantageously 3-pentenenitrile and in practical application is found as a recycle stream in the hydrocyanation process and particularly a stream from the treatment of stream 5.

Two typical streams which can be employed as extractants (line 26) contain the following compounds in the amounts indicated in Table II. Abbreviations following the name compounds are used in the following portion of the specification.

TABLE II

| Compound | Concentration (% by weight) | |
|---|---|---|
| | Stream A | Stream B |
| Cis-2-pentenenitrile (C2PN) | 0 | 2.0 |
| Cis-2-methyl-2-butene-nitrile (C2M2BN) | 2.0 | 9.0 |
| Valeronitrile (VN) | 0 | 3.0 |
| Trans-2-pentenenitrile (T2PN) | 0.5 | 5.0 |
| Trans-3-pentenenitrile (T3PN) | 88.0 | 55.0 |
| 4-pentenenitrile (4PN) | 2.0 | 3.0 |
| Cis-3-pentenenitrile (C3PN) | 3.0 | 10.0 |
| Ethyl succinonitrile (ESN) | .2 | 1.5 |
| 2-methylglutaronitrile (MGN) | 0.5 | 3.0 |
| adiponitrile (ADN) | 0.2 | 5.0 |
| Balance - Miscellaneous Organics | | |

After thorough contact of the extractant (line 26) with the sludge (line 18), the resultant mixture is directed to a suitable separator 27 via line 28. The liquid from separator 27 (line 29) is returned to the product recovery portion of the hydrocyanation process or to the hydrocyanation step. The treated solids can now be directed to dryer 30 via line 31 since the tar-forming organics have been extracted and replaced with more volatile nitriles which are readily removed without excessive degradation. Volatile materials which are driven from the solids during drying (line 32) can be condensed and combined with the solution in line 29. A typical analysis of the solution (line 29) and the volatile material from dryer 30 (line 32) is set forth below in Table III.

TABLE III

| Compound | Concentration (% by weight) | |
|---|---|---|
| | Stream 29 | Stream 32 |
| C-2-PN | 0.2 | 0 |
| C2M2BN | 2.5 | 1.2 |
| VN | 0.2 | 0 |
| T2PN | 0.2 | 0.4 |
| T3PN | 80.0 | 82.0 |
| 4PN | 1.5 | 1.5 |
| C3PN | 2.6 | 3.3 |
| ESN | 0.2 | 0.2 |
| MGN | 2.2 | 2.1 |
| ADN | 10.0 | 1.8 |

A typical (average) and range of analysis of the solids (line 33) to which the present invention is applied is set forth below.

| Compound | Concentration (% by weight) | |
|---|---|---|
| | Range | Average |
| Carbon | 60–75 | 61 |
| Hydrogen | 4–6 | 5 |
| Nitrogen | 8–15 | 12.5 |
| Nickel | 7–15 | 9 |
| Boron | 1–3 | 1.85 |
| (Triphenylborane equivalent) | | 35.2 |

The relative amounts of nickel and boron can vary from minor amounts of triphenylborane to about two moles of the borane per mole of nickel.

The solids (line 33) are transferred to pressure reactor 34 where they are contacted with an aqueous solution of a nitrogen-containing base e.g., a concentrated aqueous solution of ammonium hydroxide, introduced via line 35 in an amount sufficient to dissolve the solids, form the soluble nickel compounds, e.g., nickel cyanide ammine and to permit the formation and subsequent precipitation of the ammonia adduct of triphenylborane. As will be discussed in more detail hereinbelow the concentration of base in combination with the temperature must be high enough to prevent precipitation of the soluble nickel complex nickel hexammine tetracyanonickelate as insoluble nickel (II) cyanide monoammine. Temperatures in the range 90°–105° C are preferred. The solids (line 36) from reactor 34 consist essentially of the ammonia adduct of the triphenylborane and can be dried and/or treated to recover the free borane. The liquid (line 37) from reactor 34 is conveniently passed to flasher 38 where ammonia is removed via line 39 which causes the nickel (II) cyanide monoammine [Ni(CN)$_2$(NH$_3$)xH$_2$O] to precipitate. The precipitate (line 42) is removed from the resultant slurry (line 40) in filter 41. Nickel compounds can be recovered from the solids by several methods, e.g., thermal treatment.

Nitrogen-containing bases which are operable in the present invention include those selected from the class consisting of primary aliphatic amines having 1-10 carbon atoms, tertiary aromatic amines such as pyridine and substituted pyridines wherein the substituent groups do not react with the triarylborane and ammonia. Ammonia is preferred and the following discussion is directed to this preferred base.

The amount and/or concentration of ammonia is a critical parameter in the present process. Considering two of the principal components of the solids to which the present invention is applied, i.e., nickel and triarylborane, e.g., triphenylborane, the theoretical requirement for ammonia is four moles per mole of boron plus nickel (3 moles/mole of nickel; 1 mole/mole of boron) to form the ammonia adduct of the borane and the soluble nickel ammine complex. However, unless an excess of ammonia is present in the initial digestion, (reactor 34), the digestion can be incomplete and/or the nickel compounds can precipitate along with the ammonia adduct of the borane. This results in inefficient separation of the nickel and borane. At nickel concentrations greater than 1% by weight based upon the weight of the solution at least 6.0% by weight ammonia should be present to assure satisfactory digestion and to maintain the nickel species in solution at temperatures above about 80° C. The nickel species are more soluble at temperatures above 80° C and therefore less ammonia can be employed to realize satisfactory digestion and maintenance of the nickel in solution. However, it is desirable to employ at least the minimum amounts above stated. Preferably, the molar ratio of ammonia to nickel plus boron is initially maintained at at least 10/1 and more preferably 15–50/1 is employed. It is also preferred to maintain the concentration of ammonia in the aqueous solution in the range 15–25%.

Digestion of the catalyst solids and/or formation of the ammonia adduct of the borane is not instantaneous and is accelerated with increasing temperature. Generally reaction time of 0.5–4 hours is satisfactory. Although elevated temperatures decrease the time required for digestion and precipitation, the rate of borane degradation i.e., the loss to undesired products, is also increased as is the complexity and cost of equipment to accommodate the pressures required to maintain the reactants in the liquid phase. For convenience of operation, it is desirable to conduct the digestion/precipitation portion of the present process at a temperature in the range 80°–150° C and preferably at a temperature in the range 90°–120° C.

The following Examples are presented to illustrate but not to restrict the present invention. Parts and percentages are by weight unless otherwise specified.

EXAMPLE 1

A catalyst residue which by analysis contained 61.1% carbon, 4.9% hydrogen, 12.5% nitrogen, 8.9% nickel, and 1.85% boron (35.2% triphenylborane), weighing 1.0 gram was charged to a 10 milliliter pressure tube along with 3.5 milliliters of water and 3.5 milliliters of concentrated ammonium hydroxide (0.056 mols of ammonia). The pressure tube was sealed and the contents were rocked and heated for 1 hour at 100° C. The resultant slurry was removed from the pressure tube and the solid was recovered by vacuum filtration following which it was washed with 10 milliliters of water at room temperature and thereafter dried under vacuum at 50° C. The dry solid weighed 0.23 gram and by analysis contained 90.6% triphenylborane with an elemental analysis as follows: 80.8% carbon, 6.8% hydrogen, 5.8% nitrogen, 1.3% nickel and 4.05% boron. The recovery of triphenylborane containing approximately 1.3% nickel was 60% based upon the ammonia adduct.

The water wash as set forth hereinabove was added to the filtrate which decreased the concentration of ammonia below that required to maintain the nickel in solution with the result that a pale purple solid identified as $Ni(CN)_2(NH_3)(H_2O)_{0.5}$ precipitated and was recovered by filtration. The filtrate weighed 15.2 grams and by analysis contained 0.14% dissolved nickel.

EXAMPLE 2

The procedure of Example 1 was repeated except that 7 milliliters of concentrated ammonium hydroxide were employed. Approximately 0.34 gram of dry solid was obtained which by elemental analysis contained 80.7% carbon, 6.9% hydrogen, 6.3% nitrogen, 1.2% nickel and 4.5% boron. The recovery of triphenylborane was greater than 90% based upon the ammonia adduct.

EXAMPLES 3–7

Example 1 was repeated except that the time, temperature, and amount of ammonia were varied. The recovery of triphenylborane as the ammonia adduct was noted. The conditions and results are set forth in Table 1.

It should be noted from the comparative example that excessively long reaction time at elevated temperature can result in the severe degradation of the ammonia adduct and the subsequent loss of the borane and for this reason temperatures above 150° C are not preferred.

EXAMPLE 8

The procedure of Example 1 was repeated with a catalyst residue which by analysis contained 2.75% boron and 8.61% nickel (51.9% $\phi_3B$) except the 7 grams of an aqueous solution containing 40% by weight $CH_3NH_2$ was substituted for the ammonium hydroxide and the contents of the tube were heated at 110° C for 4 hours. The dry solid weighed 0.6288 grams and by analysis contained 75.6% $\phi_3B$ (Approximately 91.6% recovery based upon the amine adduct). When the foregoing was repeated except that the heating temperature was reduced to 100° C the recovery of $\phi_3B$ as the amine adduct increased to 95.5%.

EXAMPLE 9

The procedure of Example 1 was repeated with 0.9946 gram of the catalyst residue of Example 8 except that 4.8 grams of pyridine and 1.9 grams of $H_2O$ were substituted for the ammonium hydroxide and the contents of the tube were heated at 100° C for 4 hours. The dry solid weighed 0.7350 gram and by analysis contained 43.7% $\phi_3B$ (about 62.2% recovery based upon the pyridine adduct).

What is claimed is:

1. A process for the recovery of catalyst components from a catalyst residue which residue is obtained from the hydrocyanation of olefins using a catalyst comprising zero-valent nickel complex promoted with a triarylborane and comprises nickel cyanide, triarylborane and complexes of the foregoing, said process comprising contacting said residue with an aqueous solution containing at least 10 moles of nitrogen-containing base per mole of boron plus nickel while maintaining the concentration of said base at at least 6% to maintain the nickel in solution and to form and precipitate the basic adduct of said triarylborane and thereafter separating the precipitate from the resultant solution.

2. The process of claim 1 wherein the base is ammonia and the moles of ammonia per mole of boron plus nickel are maintained in the range 15–50.

3. The process of claim 2 wherein the concentration of said ammonia is maintained in the range 15–25%.

4. The process of claim 3 wherein the temperature is maintained in the range 90°–110° C for a period at least 30 minutes.

* * * * *

TABLE 1

| Example No. | Catalyst Residue (grams) | NH$_4$OH Concentration | Reactor Temperature ° C | Time, min. | Recovery of $(C_6H_5)_3B$ as Ammonia Adduct |
|---|---|---|---|---|---|
| 3 | 1.4 | a | 90 | 60 | 35 |
| 4 | 1.4 | a | 100 | 60 | 84 |
| 5 | 1.4 | a | 110 | 60 | ~100 |
| 6 | 1.1 | b | 90 | 360 | ~100 |
| 7 | 1.0 | c | 150 | 9 | 83 |
| Comparative | 1.0 | c | 150 | 60 | 0 | a 6 grams of 19% NH$_4$OH
b 4.7 grams of 19% NH$_4$OH
c 7 milliliters of concentrated NH$_4$OH